US010241125B2

(12) United States Patent
Yokoyama et al.

(10) Patent No.: US 10,241,125 B2
(45) Date of Patent: Mar. 26, 2019

(54) DROPLET EJECTING APPARATUS

(71) Applicant: TOSHIBA TEC KABUSHIKI KAISHA, Tokyo (JP)

(72) Inventors: Shuhei Yokoyama, Mishima Shizuoka (JP); Satoshi Kaiho, Yokohama Kanagawa (JP)

(73) Assignee: Toshiba TEC Kabushiki Kaisha, Tokyo (JP)

( * ) Notice: Subject to any disclaimer, the term of this patent is extended or adjusted under 35 U.S.C. 154(b) by 23 days.

(21) Appl. No.: 15/684,883

(22) Filed: Aug. 23, 2017

(65) Prior Publication Data

US 2018/0088142 A1    Mar. 29, 2018

(30) Foreign Application Priority Data

Sep. 23, 2016   (JP) ................................ 2016-185047

(51) Int. Cl.
*G01N 35/10* (2006.01)
*B01L 3/02* (2006.01)
*G01N 35/02* (2006.01)

(52) U.S. Cl.
CPC ........ *G01N 35/1002* (2013.01); *B01L 3/0237* (2013.01); *B01L 3/0268* (2013.01); *B01L 3/0293* (2013.01); *G01N 35/02* (2013.01); *G01N 35/109* (2013.01); *G01N 35/1074* (2013.01); *B01L 2300/0893* (2013.01); *B01L 2300/185* (2013.01); *G01N 2035/1041* (2013.01)

(58) Field of Classification Search
CPC ....... G01N 35/1002; G01N 35/02; B01L 3/02
See application file for complete search history.

(56) References Cited

U.S. PATENT DOCUMENTS

| 6,833,112 | B2 * | 12/2004 | Hoummady | ......... B01J 19/0046 |
| | | | | 347/21 |
| 6,863,375 | B2 * | 3/2005 | Makigaki | ................... B41J 2/16 |
| | | | | 347/47 |
| 8,888,217 | B2 | 11/2014 | Nishikawa et al. | |
| 2003/0086828 | A1 * | 5/2003 | Chiou | ................... B01L 3/0268 |
| | | | | 422/520 |
| 2009/0130719 | A1 * | 5/2009 | Handique | ............. B01L 3/5025 |
| | | | | 435/91.2 |

(Continued)

FOREIGN PATENT DOCUMENTS

| JP | 2004-314612 A | 11/2004 |
| JP | 2013-075490 A | 4/2013 |

OTHER PUBLICATIONS

U.S. Appl. No. 15/176,265, filed Jun. 8, 2016 (First Inventor: Ryutaro Kusunoki).

(Continued)

*Primary Examiner* — Jewel V Dowtin
(74) *Attorney, Agent, or Firm* — Kim & Stewart LLP (57) ABSTRACT

According to one embodiment, a droplet ejecting apparatus includes a solution holding container having a solution inlet for receiving a solution on a first side and a plurality of solution outlets on a second side, a plurality of droplet ejecting arrays, each droplet ejecting array being respectively connected to one solution outlet in the plurality of solution outlets, and a first nozzle group in each droplet ejecting array fluidly connected to the respective one solution outlet via a pressure chamber structure.

19 Claims, 9 Drawing Sheets

(56) References Cited

U.S. PATENT DOCUMENTS

2012/0176447 A1* 7/2012 Otokita .................. B41J 2/055
                                                                    347/40
2014/0253640 A1   9/2014 Yokoyama et al.
2018/0088142 A1* 3/2018 Yokoyama ......... G01N 35/1074

OTHER PUBLICATIONS

Japanese Office Action dated Jan. 9, 2018, filed in the counterpart Japanese Patent Application No. 2015-116080 (12 pages) (with English Translation).

* cited by examiner

DROPLET EJECTING APPARATUS

CROSS-REFERENCE TO RELATED APPLICATION

This application is based upon and claims the benefit of priority from Japanese Patent Application No. 2016-185047, filed Sep. 23, 2016, the entire contents of which are incorporated herein by reference.

FIELD

Embodiments described herein relate generally to a droplet ejecting apparatus.

BACKGROUND

Fluid dispensing in a range of picoliters (pL) to microliters (μL) is often used in biological and pharmaceutical research and development, medical diagnosis and examination, or agricultural testing. For example, in studying a dose-response effect of chemotherapy, fluid dispensing with a low volume is an important task for determining the concentration of a candidate compound required to effectively attack cancer cells.

In such dose-response experiments, candidate compounds are prepared at many different concentrations in the wells of a multi-well plate to determine an effective concentration. An existing on-demand type droplet ejecting apparatus is used for the above application. For example, the droplet ejecting apparatus includes a storage container that holds a solution, a nozzle that ejects the solution, a pressure chamber that is disposed between the storage container and the nozzle, and an actuator that controls pressure of the solution inside the pressure chamber to eject the solution from the nozzle.

In the droplet ejecting apparatus, the volume of one droplet ejected from an individual nozzle is on the order of a picoliter (pL). By controlling the total number of droplets ejected into each well, the droplet ejecting apparatus supplies an amount of fluid in a range of picoliters to microliters into each well. Therefore, the droplet ejecting apparatus is generally suitable for dose-response experiments when dispensing the candidate compounds at various concentrations or when dispensing in very small amounts.

A multiwell plate (also referred to as a microplate) normally used in this context has 1,536 wells (hereinafter, this multiwell plate may be referred to as a 1,536 well plate). Efforts have also been made to use a microplate having 3,456 wells (hereafter, referred to as a 3,456 well plate) and a microplate having 6,144 holes (hereinafter, referred to as a 6,144 well plate). However, in microplates having more than 1,536 wells, the wells must typically be very densely arranged. Though, it is possible to improve experimental evaluation efficiency by increasing the number of samples and to improve reagent utilization efficiency since the volume of the wells is usually smaller.

DETAILED DESCRIPTION

In general, according to one embodiment, a droplet ejecting apparatus includes a solution holding container having a solution inlet for receiving a solution on a first side and a plurality of solution outlets on a second side, a plurality of droplet ejecting arrays, each droplet ejecting array being respectively connected to one solution outlet in the plurality of solution outlets, and a first nozzle group in each droplet ejecting array fluidly connected to the respective one solution outlet via a pressure chamber structure.

Hereinafter, example embodiments will be described with reference to the drawings. Each drawing is a schematic view for illustrating the embodiments and facilitating understanding thereof. The shape, dimension, and ratio may be different from those of the actual one. Design thereof can be changed as appropriate.

One object of certain example embodiments described herein is to provide a droplet ejecting apparatus which completes a dropping task in a short time to prevent the concentration of a compound in a storage container from being changed due to solution/solvent volatilization when a tested compound has been dissolved in a highly volatile solution/solvent. Over time, the solution components/solvent may evaporate or otherwise volatize from the liquid phase into the vapor phase in the storage container during the process of dropping the solution into the individual wells of 1,536/3,456/6,144 well plates.

When a microplate having many wells, such as 1,536/3,456/6,144 well plates, is used in an on-demand type of droplet ejecting apparatus, if the solution is dropped separately into each well, it takes a long time to drop the solution into all of the wells in the microplate. Therefore, if a highly volatile solution is being dropped into the wells, there is a possibility that the solution in a storage container may be volatilized and solute concentration may be changed during the time of a dropping operation.

A task of dispensing compounds having different concentrations to each well is carried out by controlling the dispensed number of droplets of the solution into each well. In this task, if the concentration of the solution contained in the solution holding container changes during the dispensing process, the concentration of the solution dispensed into each well might not be accurately known. Therefore, when the on-demand type of droplet ejecting apparatus drops the solution onto the microplate having 1,536 wells or more, the droplet ejecting apparatus needs to complete the solution dispensing process for all of the wells in a short time so as to limit the concentration of the solution in the solution holding container being changed due to volatilization of solution/solvent.

First Embodiment

Figure 1:
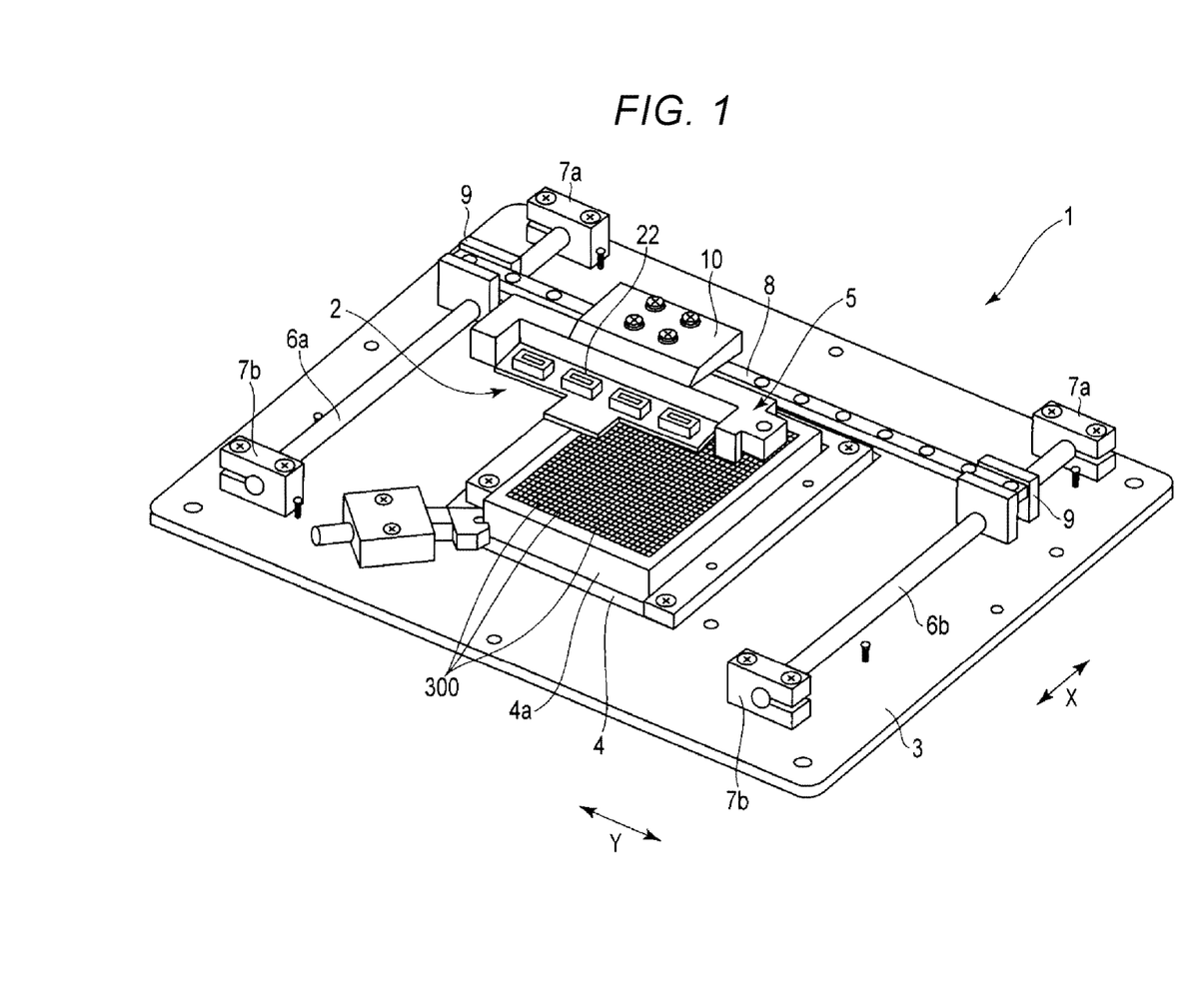
FIG. 1 is a schematic perspective view of a solution dropping apparatus equipped with a droplet ejecting apparatus according to a first embodiment.
Figure 2:
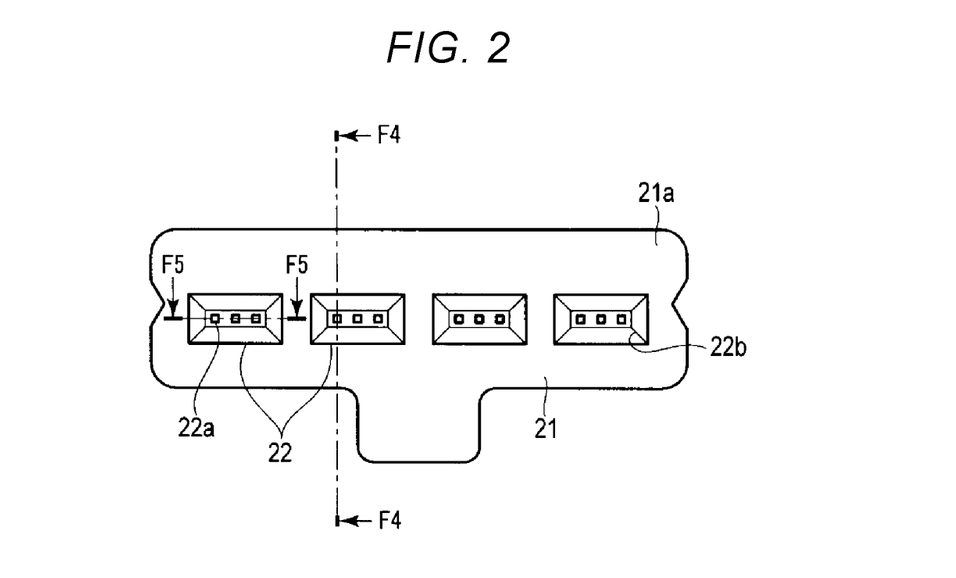
FIG. 2 is a top view of a droplet ejecting apparatus according to the first embodiment.
Figure 3:
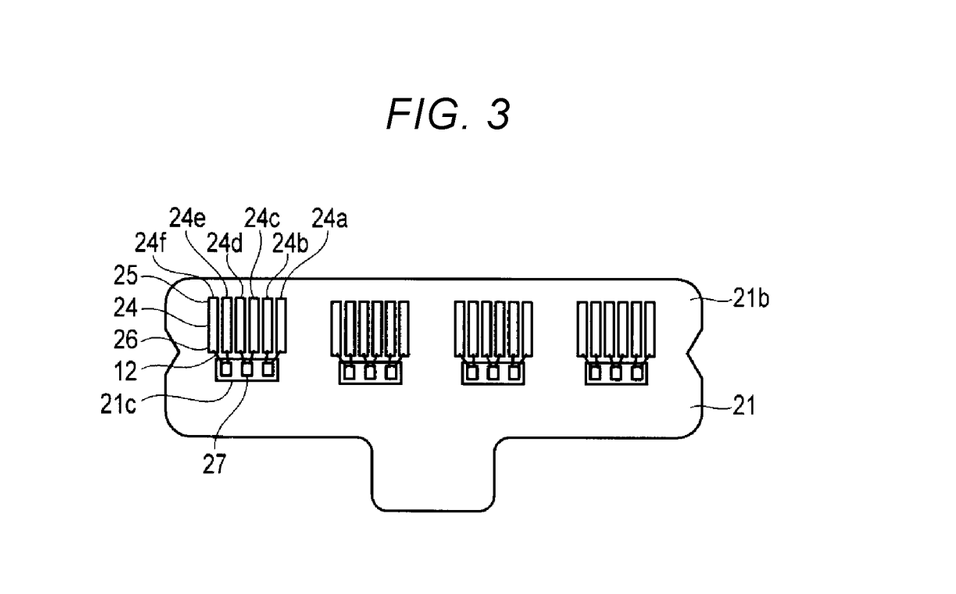
FIG. 3 is a bottom view of a droplet ejecting apparatus.
Figure 4:
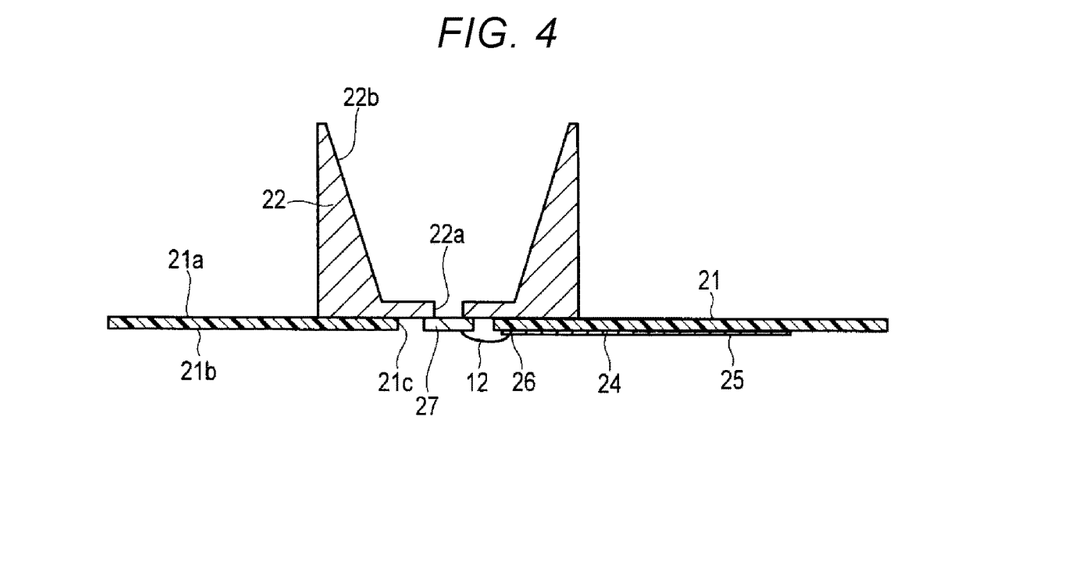
FIG. 4 is a cross-sectional view taken along line F4-F4 in FIG. 2.
Figure 5:
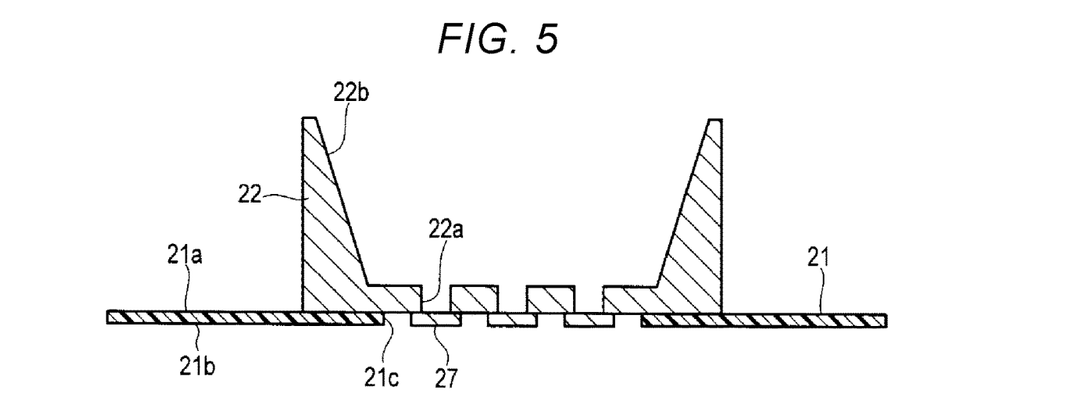
FIG. 5 is a cross-sectional view taken along line F5-F5 in FIG. 2.
Figure 6:
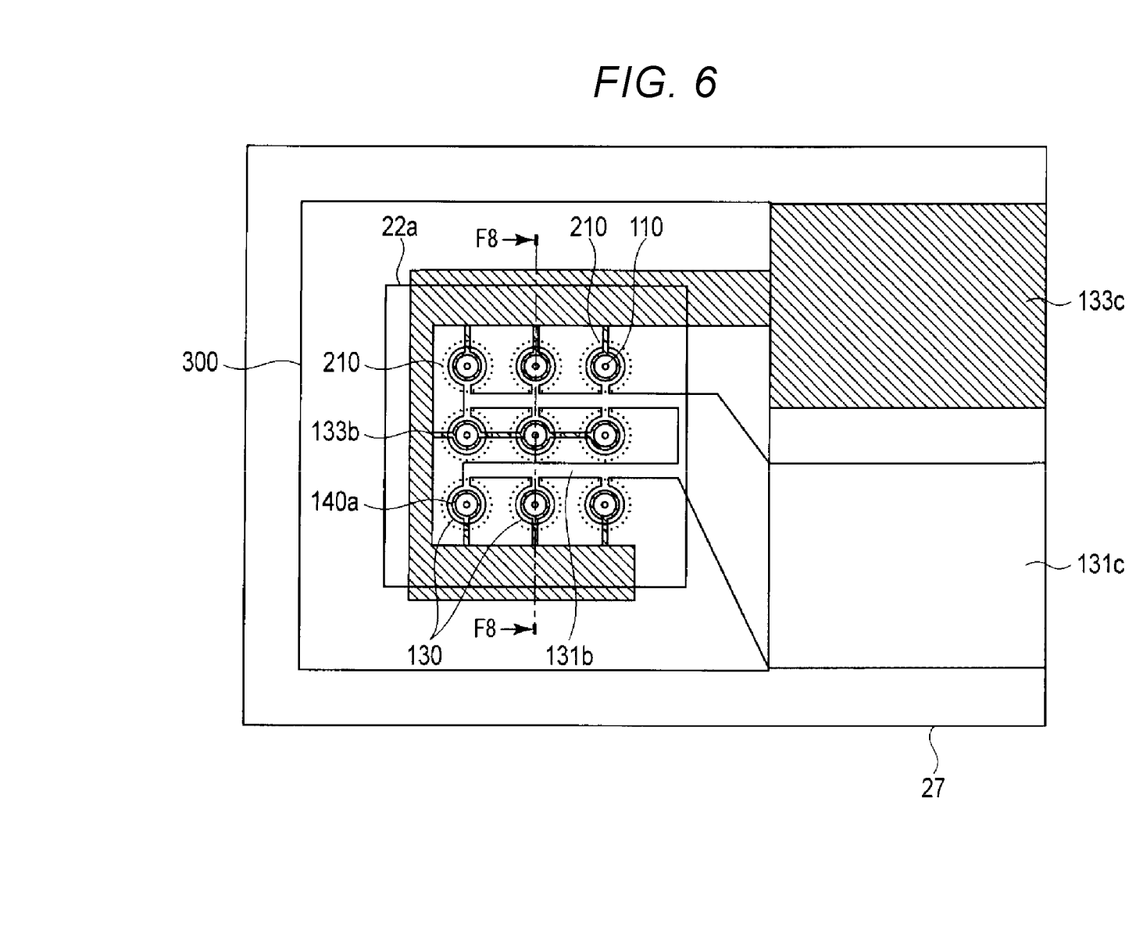
FIG. 6 is a plan view of a droplet ejecting array of a droplet ejecting apparatus.
Figure 7:
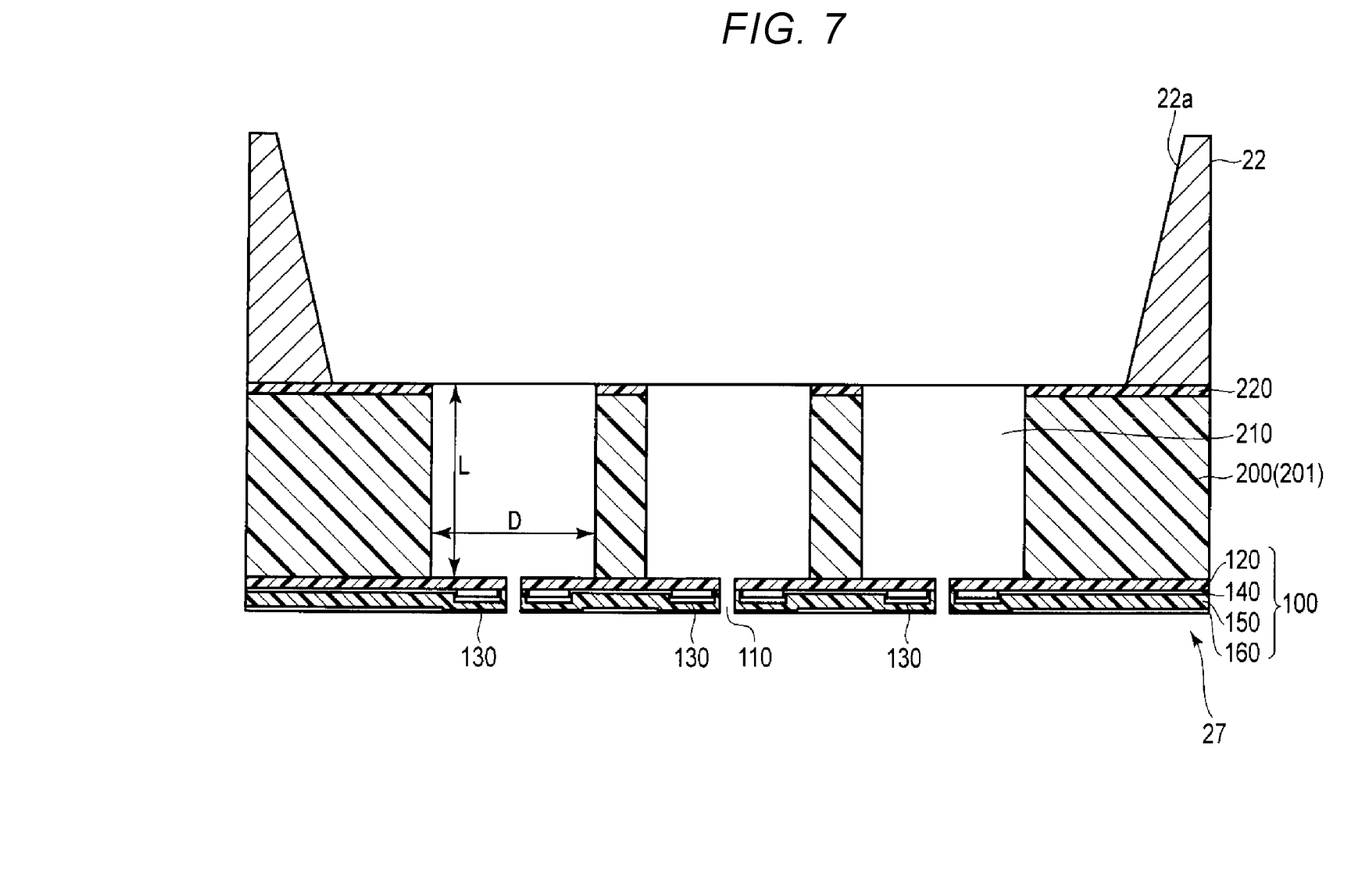
FIG. 7 is a cross-sectional view taken along line F8-F8 in FIG. 6.
Figure 8:
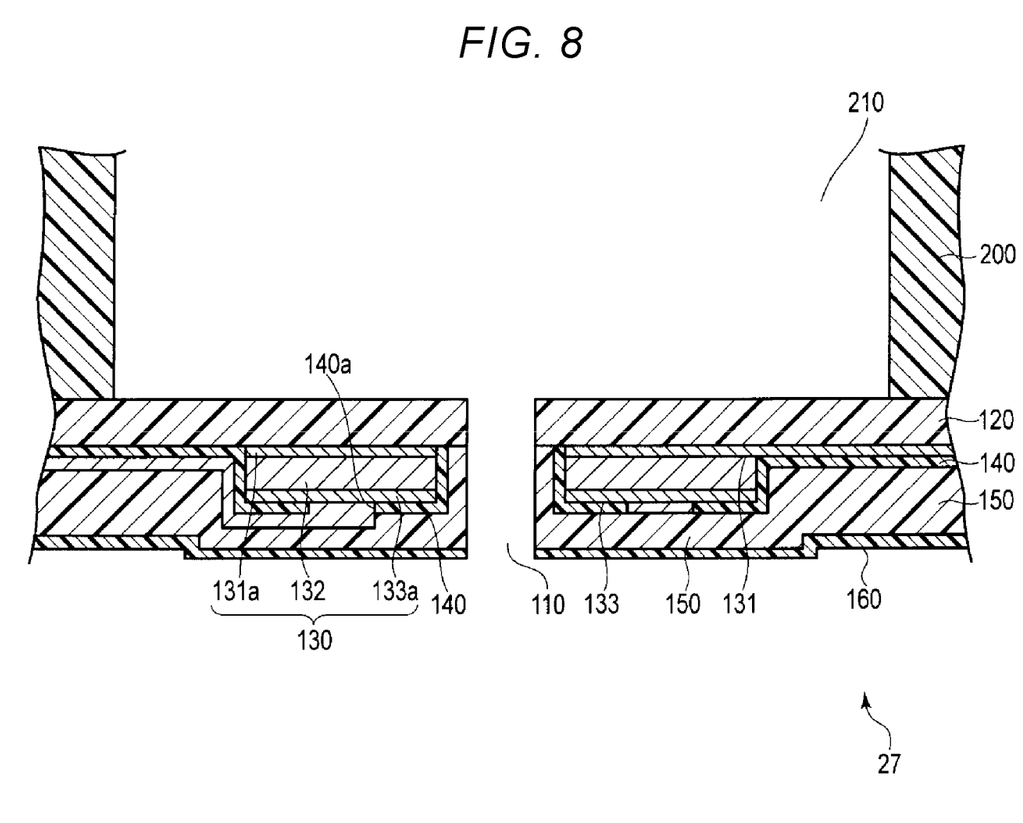
FIG. 8 is a longitudinal sectional view of a nozzle in a droplet ejecting apparatus.
Figure 9:
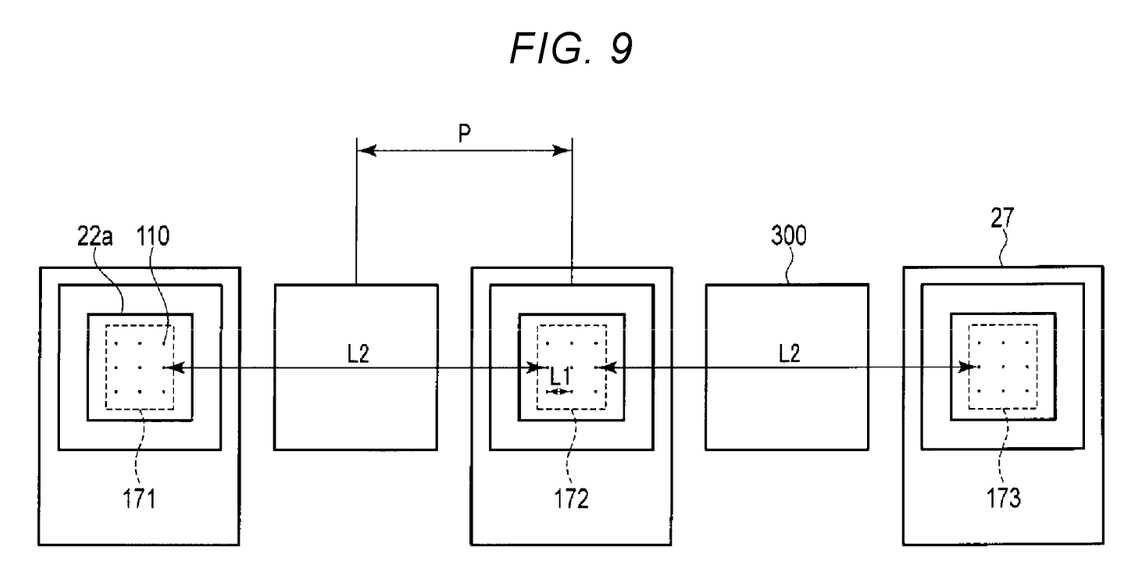
FIG. 9 is a plan view of a position relationship between a nozzle communicating with one solution holding container and a well opening of a 1,536 well microplate in a droplet ejecting apparatus.

An example of a droplet ejecting apparatus according to a first embodiment will be described with reference to FIGS. 1 to 9. FIG. 1 is a perspective view of a solution dropping apparatus 1 including a droplet ejecting apparatus 2 according to the first embodiment. FIG. 2 is a top view of the droplet ejecting apparatus 2. FIG. 3 is a bottom view of a surface from which the droplet ejecting apparatus 2 ejects a droplet. FIG. 4 is a cross-sectional view taken along line F4-F4 in FIG. 2. FIG. 5 is a cross-sectional view taken along line F5-F5 in FIG. 2. FIG. 6 is a plan view of a droplet ejecting array 27 of the droplet ejecting apparatus 2 according to the first embodiment. FIG. 7 is a cross-sectional view taken along line F8-F8 in FIG. 6. FIG. 8 is a longitudinal sectional view of a nozzle 110 in the droplet ejecting apparatus 2. FIG. 9 is a plan view of a position relationship between the nozzle communicating with one solution holding container and a well opening of a 1,536 well microplate.

The solution dropping apparatus 1 has a rectangular plate-shaped base 3 and a droplet ejecting apparatus mounting module 5. In these examples, a solution is dropped onto the microplate 4 having 1,536 wells. In the microplate 4 having 1,536 wells, well openings 300 having 1,536 holes are formed on a surface of a flat plate-shaped microplate body 4a.

The microplate 4 is fixed to the base 3. On either side of the microplate 4 on the base 3, right and left X-direction guide rails 6a and 6b extending in an X-direction are installed. Both end portions of the respective X-direction guide rails 6a and 6b are fixed to fixing bases 7a and 7b protruding on the base 3.

A Y-direction guide rail 8 extending in a Y-direction is installed between the X-direction guide rails 6a and 6b. Both ends of the Y-direction guide rail 8 are respectively fixed to an X-direction moving table 9 which can slide in the X-direction along the X-direction guide rails 6a and 6b.

A Y-direction moving table 10 is disposed on the Y-direction guide rail 8 and can move the droplet ejecting apparatus mounting module 5 in the Y-direction along the Y-direction guide rail 8. The droplet ejecting apparatus mounting module 5 is mounted on the Y-direction moving table 10. The droplet ejecting apparatus 2 is fixed to the droplet ejecting apparatus mounting module 5. In this manner, an operation of the Y-direction moving table 10 moving in the Y-direction along the Y-direction guide rail 8 can be combined with an operation of the X-direction moving table 9 moving in the X-direction along the X-direction guide rails 6a and 6b. Accordingly, the droplet ejecting apparatus 2 is supported so as to be movable to any position in XY-directions which are orthogonal to each other.

The droplet ejecting apparatus 2 has a flat plate-shaped electrical board 21. As illustrated in FIG. 2, a plurality of (e.g., four in the first embodiment) solution holding containers 22 are juxtaposed along the Y-direction on a front surface side, also referred to as a first surface 21a, of the electrical board 21. As illustrated in FIG. 4, the solution holding container 22 has a bottomed and recessed shape whose upper surface is open. As illustrated in FIG. 5, three lower surface openings 22a which serve as solution outlets at the center position are formed in a bottom portion of the solution holding container 22. An opening area of an upper surface opening 22b is larger than an opening area of the lower surface opening 22a serving as the solution outlet.

As illustrated in FIG. 3, a rectangular opening 21c is formed in the electrical board 21 in each solution holding container 22. Each opening 21c is a through-hole that is larger than the lower surface opening 22a, which serves as the solution outlet of the solution holding container 22. As illustrated in FIGS. 4 and 5, a bottom portion of the solution holding container 22 is bonded and fixed to the first surface 21a of the electrical board 21. Here, the lower surface opening 22a, serving as the solution outlet of the solution holding container 22, is located inside the opening 21c of the electrical board 21.

An electrical board wiring 24 is patterned on a rear surface side, also referred to as a second surface 21b, of the electrical board 21. Each rectangular opening 21c is connected to wiring patterns 24a, 24c, and 24e and wiring patterns 24b, 24d, and 24f. The wiring patterns 24a, 24c, and 24e are respectively connected to three terminal portions 131c of a lower electrode 131. The wiring patterns 24b, 24d, and 24f are respectively connected to three terminal portions 133c of an upper electrode 133.

One end portion of the electrical board wiring 24 has a control signal input terminal 25 for inputting a control signal from the outside. The other end portion of the electrical board wiring 24 includes an electrode terminal connector 26 for connecting the lower electrode terminal portion 131c and the upper electrode terminal portion 133c which are formed in the droplet ejecting array 27, also referred to as a second board, illustrated in FIG. 6.

As illustrated in FIG. 5, three droplet ejecting arrays 27 are bonded and fixed to the lower surfaces of the solution holding containers 22 so that each droplet ejecting array 27 covers a different one of the openings 22a of the solution holding containers 22. The three droplet ejecting arrays 27 are disposed at positions corresponding to the opening 21c in the electrical board 21.

As illustrated in FIG. 7, the droplet ejecting array 27 has a nozzle plate 100 and a pressure chamber structure 200, which are stacked on each other. The nozzle plate 100 has a plurality of the nozzles 110 for ejecting the solution. As illustrated in FIG. 6, in the first embodiment, a plurality of the nozzles 110 is arranged in 3 by 3 rows to be within the one well opening 300 of a 1,536 well microplate 4. Here, each set of the nine nozzles 110 arranged in 3 by 3 rows is referred to as a nozzle group. That is, as illustrated in FIG. 9, the droplet ejecting apparatus 2 in the first embodiment has three nozzle groups 171, 172, and 173 (each having nine nozzles 110). In this manner, the droplet ejecting apparatus 2 has 27 nozzles 110. All of the 27 nozzles 110 communicate with the one solution holding container 22.

When the droplet ejecting apparatus 2 is disposed directly above a well opening 300 of the 1,536 well microplate 4, each of the three nozzle groups 171, 172, and 173 is disposed inside a well opening 300 of the 1,536 well microplate 4. Therefore, all of the 27 nozzles 110 communicating with one solution holding container 22 are disposed inside a well opening 300 of the 1,536 well microplate 4, though each of the three nozzle groups 171, 172, 173 is above a different well opening 300 of the 1,536 well microplate 4 (see FIG. 9).

A pitch P of the well openings 300 of a 1,536 well microplate 4 is 2.25 mm. In general, the well opening 300 of a 1,536 well microplate 4 has a square shape in which each side is approximately 1.7 mm. A center distance L1 between the adjacent nozzles 110 in the one nozzle group 171 (alternatively 172 or 173) in FIG. 9, which are arranged in 3 by 3 rows, is 0.25 mm. Therefore, the distance between the centers of the nozzles 110 within nozzle group 171 (alternatively 172 or 173) is 0.5 mm in the X-direction and 0.5 mm in the Y-direction. The area covered by one nozzle group 171 (alternatively 172 or 173) is thus smaller than the opening area of each well opening 300 of a 1,536 well microplate 4.

A separation distance L2 between closest nozzles in adjacent nozzle groups 171 and 172, or 172 and 173 is 4 mm. The distance L2 between the closest nozzles in adjacent nozzle groups 171 and 172, or 172 and 173 is longer than the distance L1 (=0.25 mm) between the adjacent nozzles 110 within one nozzle group 171 (alternatively 172 or 173). Thus, each of the nozzles 110 of the droplet ejecting array 27 can be disposed inside a well opening 300 of a 1,536 well microplate 4 simultaneously.

As illustrated in FIG. 7, the nozzle plate 100 includes a drive element 130 serving as a drive unit, a protective film 150 serving as a protective layer, and a fluid repellent film 160, on a diaphragm 120. The actuator corresponds to the diaphragm 120 and the drive element 130. In some embodiments, the diaphragm 120 may be integrated with the pressure chamber structure 200. For example, when the chamber structure 200 is manufactured on a silicon wafer 201 by a heat treatment in an oxygen atmosphere, a $SiO_2$ (silicon oxide) film is formed on a surface of the silicon wafer 201. The diaphragm 120 may be the $SiO_2$ (silicon oxide) film on the surface of the silicon wafer 201 formed by the heat treatment in the oxygen atmosphere. The diaphragm 120 may be formed using a chemical vapor deposition (CVD) method by depositing the $SiO_2$ (silicon oxide) film on the surface of the silicon wafer 201.

It is preferable that the film thickness of the diaphragm 120 is within a range of 1 to 30 μm. The diaphragm 120 may be of a semiconductor material such as a SiN (silicon nitride) or $Al_2O_3$ (aluminum oxide).

The drive element 130 is formed for each of the nozzles 110. The drive element 130 has an annular shape surrounding the nozzle 110. A shape of the drive element 130 is not limited, and may be a C-shape obtained by partially cutting the annular shape, for example. As illustrated in FIG. 8, the drive element 130 includes an electrode portion 131a of the lower electrode 131 and an electrode portion 133a of the upper electrode 133, interposing a piezoelectric film 132 serving as a piezoelectric body. The electrode portion 131a, the piezoelectric film 132, and the electrode portion 133a are circular coaxial with the nozzle 110 and have similar diameters.

The lower electrode 131 includes a plurality of circular electrode portions 131a each coaxial with a corresponding circular nozzle 110. For example, the nozzle 110 may have a diameter of 20 μm, and the electrode portion 131a may have an outer diameter of 133 μm and an inner diameter of 42 μm. As illustrated in FIG. 6, the lower electrode 131 includes a wiring portion 131b which connects the plurality of electrode portions 131a to one another. An end portion of the wiring portion 131b includes a terminal portion 131c. In FIG. 6, the electrode portion 131a of the lower electrode 131 and the electrode portion 133a of the upper electrode 133 are overlaid.

The drive element 130 includes the piezoelectric film 132 formed of a piezoelectric material having the thickness of 2 μm, for example, on the electrode portion 131a of the lower electrode 131. The piezoelectric film 132 may be formed of PZT (Pb(Zr, Ti)$O_3$: lead titanate zirconate). For example, the piezoelectric film 132 is coaxial with the nozzle 110, and has an annular shape whose outer diameter is 133 μm and inner diameter is 42 μm, which is the same shape as the shape of the electrode portion 131a. The film thickness of the piezoelectric film 132 is set to a range of approximately 1 to 30 μm. For example, the piezoelectric film 132 may be of a piezoelectric material such as PTO (PbTiO$_3$: lead titanate), PMNT (Pb(Mg$_{1/3}$Nb$_{2/3}$)O$_3$—PbTiO$_3$), PZNT (Pb(Zn$_{1/3}$Nb$_{2/3}$)O$_3$—PbTiO$_3$), ZnO, and AlN.

The piezoelectric film 132 generates polarization in a direction parallel to a thickness of the piezoelectric film 132. If an electric field in the direction of the polarization is applied to the piezoelectric film 132, the piezoelectric film 132 expands and contracts in a direction orthogonal to the electric field. In other words, the piezoelectric film 132 contracts or expands in a direction orthogonal to the film thickness.

The upper electrode 133 of the drive element 130 is coaxial with the nozzle 110 on the piezoelectric film 132, and has an annular shape whose outer diameter is 133 μm and inner diameter is 42 μm, which is the same shape as the shape of the piezoelectric film 132. As illustrated in FIG. 6, the upper electrode 133 includes a wiring portion 133b which connects the plurality of the electrode portions 133a to one another. An end portion of the wiring portion 133b includes a terminal portion 133c. If a predetermined voltage is applied to the upper electrode 133, a voltage control signal is applied to the lower electrode 131.

For example, the lower electrode 131 may be formed with a thickness of 0.5 μm by stacking Ti (titanium) and Pt (platinum) using a sputtering method. The film thickness of the lower electrode 131 is in a range of approximately 0.01 to 1 μm. The lower electrode 131 may be of other materials such as Ni (nickel), Cu (copper), Al (aluminum), Ti (titanium), W (tungsten), Mo (molybdenum), Au (gold), and SrRuO$_3$ (strontium ruthenium oxide). The lower electrode 131 may also be of various stacked metal materials.

The upper electrode 133 is formed of a Pt thin film. The thin film is formed using a sputtering method, and the film thickness is set to 0.5 μm. As other electrode materials of the upper electrode 133, Ni, Cu, Al, Ti, W, Mo, Au, and SrRuO$_3$ can be used. As another film formation method, vapor deposition and plating can be used. The upper electrode 133 may be of various stacked metal materials. The desirable film thickness of the upper electrode 133 is 0.01 to 1 μm.

The nozzle plate 100 includes the insulating film 140 which insulates the lower electrode 131 and the upper electrode 133 from each other. For example, SiO$_2$ (silicon oxide) having the thickness of 0.5 μm is used for the insulating film 140. In a region proximate to the drive element 130, the insulating film 140 covers the periphery of the electrode portion 131a, the piezoelectric film 132, and the electrode portion 133a. The insulating film 140 covers the wiring portion 131b of the lower electrode 131. The insulating film 140 covers the diaphragm 120 in the region proximate to the wiring portion 133b of the upper electrode 133. The insulating film 140 includes a contact portion 140a which electrically connects the electrode portion 133a and the wiring portion 133b of the upper electrode 133 to each other.

The nozzle plate 100 includes the protective film 150 formed of polyimide, for example, which protects the drive element 130. The protective film 150 includes a cylindrical solution passage 141 communicating with the nozzle 110 in the diaphragm 120. The solution passage 141 has the diameter of 20 μm which is the same as the diameter of the nozzle 110 in the diaphragm 120.

The protective film 150 may be of other insulating materials such as other resins or ceramics. Examples of other resins include ABS (acrylonitrile butadiene styrene), polyacetal, polyamide, polycarbonate, and polyether sulfone. For example, ceramics include zirconia, silicon carbide, silicon nitride, and silicon oxide. The film thickness of the protective film 150 is in a range of approximately 0.5 to 50 μm.

For selecting the material for the protective film 150, the following factors are considered such as the Young's modulus, heat resistance, insulation quality, which determines influence of solution deterioration due to contact with the upper electrode 133 when the drive element 130 is driven in a state of using a highly conductive solution, the coefficient of thermal expansion, smoothness, and wettability to solution.

The nozzle plate 100 includes a fluid repellent film 160 which covers the protective film 150. The fluid repellent film 160 is formed, for example, by spin-coating a silicone resin so as to have a property of repelling a solution. The fluid repellent film 160 can be formed of a material, such as a fluorine-containing resin. The thickness of the fluid repellent film 160 is in a range of approximately 0.5 to 5 μm.

The pressure chamber structure 200 is formed using silicon wafer 201 having the thickness of 525 μm, for example. The pressure chamber structure 200 includes a warp reduction film 220 serving as a warp reduction layer on a surface opposite to the diaphragm 120. The pressure chamber structure 200 includes a pressure chamber 210 which penetrates the warp reduction film 220, reaches a position of the diaphragm 120, and communicates with the nozzle 110. The pressure chamber 210 is formed in a circular shape having the diameter of 190 μm which is located coaxially with the nozzle 110, for example. The shape and size of the pressure chamber 210 are not limited.

However, in the first embodiment, the pressure chamber 210 includes an opening which communicates with the opening 22a of the solution holding container 22. It is preferable that a size L in a depth direction of the pressure chamber 210 is larger than a size D in a width direction of the opening of the pressure chamber 210. Accordingly, due to the oscillation of the diaphragm 120 of the nozzle plate 100, the pressure applied to the solution contained in the pressure chamber 210 is delayed in escaping to the solution holding container 22.

A side on which the diaphragm 120 of the pressure chamber 210 is disposed is referred to as a first surface of the pressure chamber structure 200, and a side on which the warp reduction film 220 is disposed is referred to as a second surface of the pressure chamber structure 200. The solution holding container 22 is bonded to the warp reduction film 220 side of the pressure chamber structure 200 by using an epoxy adhesive, for example. The pressure chamber 210 of the pressure chamber structure 200 communicates with the opening 22a of the solution holding container 22 through the opening on the warp reduction film 220 side. An opening area of the opening 22a of the solution holding container 22 is larger than a total area of openings of the pressure chambers 210 in the droplet ejecting array 27 connecting to the opening 22a of the solution holding container 22. Therefore, all of the pressure chambers 210 formed in the droplet ejecting array 27 communicate with the opening 22a of the solution holding container 22.

For example, the warp reduction film 220 is formed in such a way that the silicon wafer 201 is subjected to heat treatment in an oxygen atmosphere, and employs the $SiO_2$ (silicon oxide) film having a thickness of 4 μm which is formed on the surface of the silicon wafer 201. The warp reduction film 220 may be formed by depositing a $SiO_2$ (silicon oxide) film on the surface of the silicon wafer 201 using a chemical vapor deposition method (CVD method). The warp reduction film 220 reduces warp occurring in the droplet ejecting array 27.

The warp reduction film 220 is on the side opposite to the side where the diaphragm 120 is formed on the silicon wafer 201. The warp reduction film 220 reduces the warp of the silicon wafer 201 which is caused by a difference in film stress between the pressure chamber structure 200 and the diaphragm 120 and further a difference in film stress between various configuration films of the drive element 130. The warp reduction film 220 reduces the warp of the droplet ejecting array 27 if the droplet ejecting array 27 is prepared using a deposition process.

The material and the film thickness of the warp reduction film 220 may be different from those of the diaphragm 120. However, if the warp reduction film 220 employs the material and the film thickness which are the same as those of the diaphragm 120, the difference in the film stress between the diaphragms 120 on both sides of the silicon wafer 201 is the same as the difference in the film stress between the warp reduction films 220. If the warp reduction film 220 employs the material and the film thickness which are the same as those of the diaphragm 120, the warp occurring in the droplet ejecting array 27 may be more effectively reduced.

The diaphragm 120 is deformed in the thickness direction by the operation of the drive element 130 having a planar shape. The droplet ejecting apparatus 2 ejects the solution supplied to the nozzle 110 due to a pressure change in the pressure chamber 210 of the pressure chamber structure 200 which is caused by the deformation of the diaphragm 120.

An example of a manufacturing method of the droplet ejecting array 27 will be described. In the droplet ejecting array 27, the $SiO_2$ (silicon oxide) film is first formed on both entire surfaces of the silicon wafer 201 for forming the pressure chamber structure 200. The $SiO_2$ (silicon oxide) film formed on one surface of the silicon wafer 201 is used as the diaphragm 120. The $SiO_2$ (silicon oxide) film formed on the other surface of the silicon wafer 201 is used as the warp reduction film 220.

For example, the $SiO_2$ (silicon oxide) films are formed on both surfaces of the disc-shaped silicon wafer 201 using a thermal oxidation method in which heat treatment is performed in an oxygen atmosphere using a batch type reaction furnace. Next, the plurality of nozzle plates 100 and pressure chambers 210 are formed on the disc-shaped silicon wafer 201 using a deposition process. After the nozzle plate 100 and the pressure chamber 210 are formed, the disc-shaped silicon wafer 201 is cut and separated into the plurality of pressure chamber structures 200 integrated with the nozzle plate 100. The plurality of droplet ejecting arrays 27 can be mass-produced at once using the disc-shaped silicon wafer 201. The silicon wafer 201 may not have a disc shape. A silicon wafer 201 may be used so as to separately form the nozzle plate 100 and the pressure chamber structure 200 which are integrated with each other.

The diaphragm 120 formed on the silicon wafer 201 is patterned using an etching mask so as to form the nozzle 110. The patterning may use a photosensitive resist as a material of the etching mask. After the photosensitive resist is coated on the surface of the diaphragm 120, exposure and development are performed to form the etching mask in which the opening corresponding to the nozzle 110 is patterned. The diaphragm 120 is subjected to dry etching from above the etching mask until the dry etching reaches the pressure chamber structure 200 so as to form the nozzle 110. After the nozzle 110 is formed in the diaphragm, the etching mask is removed using a stripping solution, for example.

Next, the drive element 130, the insulating film 140, the protective film 150, and the fluid repellent film 160 are formed on the surface of the diaphragm 120 having the nozzle 110 formed thereon. In forming the drive element 130, the insulating film 140, the protective film 150, and the fluid repellent film 160, a film forming process and a patterning process are repeatedly performed. The film forming process is performed using a sputtering method, a CVD method, or a spin coating method. For example, the patterning is performed in such a way that the etching mask is formed on the film using the photosensitive resist and the etching mask is removed after the film material is etched.

The materials of the lower electrode 131, the piezoelectric film 132, and the upper electrode 133 are stacked on the diaphragm 120 so as to form a film. As the material of the lower electrode 131, a Ti (titanium) film and a Pt (platinum) film are sequentially formed using a sputtering method. The Ti (titanium) and Pt (platinum) films may be formed using a vapor deposition method or plating.

As the material of the piezoelectric film 132, PZT (Pb(Zr, Ti) $O_3$: lead titanate zirconate) is deposited on the lower electrode 131 using an RF magnetron sputtering method at the board temperature of 350° C. When the PZT film is subjected to heat treatment at 500° C. for 3 hours after the PZT film is formed, the PZT film can obtain satisfactory piezoelectric performance. The PZT film may be formed using a chemical vapor deposition (CVD) method, a sol-gel method, an aerosol deposition (AD) method, or a hydrothermal synthesis method.

As the material of the upper electrode 133, the Pt (platinum) film may be deposited on the piezoelectric film 132 using the sputtering method. On the deposited Pt (platinum) film, an etching mask is prepared to leave the lower electrode 131 and the electrode portion 133a of the upper electrode 133 and the piezoelectric film 132. The Pt (platinum) and PZT (Pb (Zr, Ti)$O_3$: lead titanate zirconate) films are removed by etching from above the etching mask, thereby forming the electrode portion 133a of the upper electrode 133 and the piezoelectric film 132.

Next, the etching mask which leaves the electrode portion 131a of the lower electrode 131, the wiring portion 131b, and the terminal portion 131c is formed on the lower electrode 131 on which the electrode portion 133a of the upper electrode 133 and the piezoelectric film 132 are formed. Etching is performed from above the etching mask, and the Ti (titanium) and Pt (platinum) films are removed so as to form the lower electrode 131.

As the material of the insulating film 140, the $SiO_2$ (silicon oxide) film is formed on the diaphragm 120 on which the lower electrode 131, the electrode portion 133a of the upper electrode 133, and the piezoelectric film 132 are formed. For example, the $SiO_2$ (silicon oxide) film may be formed at low temperature using the CVD method so as to obtain satisfactory insulating performance. The formed $SiO_2$ (silicon oxide) film is patterned so as to form the insulating film 140.

As the material of the wiring portion 133b and the terminal portion 133c of the upper electrode 133, Au (gold) is deposited using the sputtering method on the diaphragm 120 having the insulating film 140 formed thereon. The Au (gold) film may be formed using the vapor deposition method or the CVD method, or plating. The etching mask which leaves the electrode wiring portion 133b and the terminal portion 133c of the upper electrode 133 is formed on the deposited Au (gold) film. Etching is performed from above the etching mask, the Au (gold) film is removed so as to form the electrode wiring portion 133b and the terminal portion 133c of the upper electrode 133.

A polyimide film which may be the material of the protective film 150 is formed on the diaphragm 120 having the upper electrode 133 formed thereon. The polyimide film is formed in such a way that a solution containing a polyimide precursor is coated on the diaphragm 120 using a spin coating method and thermal curing is performed by baking so as to remove a solvent. The formed polyimide film is patterned so as to form the protective film 150 which exposes the solution passage 141, the terminal portion 131c of the lower electrode 131, and the terminal portion 133c of the upper electrode 133.

A silicone resin film which may be the material of the fluid repellent film 160 is coated on the protective film 150 using a spin coating method, and thermal curing is performed by baking so as to remove the solvent. The formed silicone resin film is then patterned so as to form the fluid repellent film 160 which exposes the nozzle 110, the solution passage 141, the terminal portion 131c of the lower electrode 131, and the terminal portion 133c of the upper electrode 133.

For example, a rear surface protective tape for chemical mechanical polishing (CMP) of the silicon wafer 201 may adhere onto the fluid repellent film 160 as a cover tape so as to protect the fluid repellent film 160 and the pressure chamber structure 200 can be patterned. The etching mask which exposes the pressure chamber 210 with the diameter of 190 μm is formed on the warp reduction film 220 of the silicon wafer 201. First, the warp reduction film 220 is subjected to dry etching using mixed gas of $CF_4$ (carbon tetrafluoride) and $O_2$ (oxygen). Next, for example, vertical deep dry etching preferentially for the silicon wafer is performed using mixed gas of $SF_6$ (sulfur hexafluoride) and $O_2$. The dry etching is stopped at a position in contact with the diaphragm 120, thereby forming the pressure chamber 210 in the pressure chamber structure 200.

The etching for forming the pressure chamber 210 may be performed by a wet etching method using a liquid etchant or a dry etching method using plasma. After the etching is completed, the etching mask is removed. A cover tape adhering onto the fluid repellent film 160 is irradiated with ultraviolet light so as to weaken adhesiveness therebetween, and the cover tape is detached from the fluid repellent film 160. The disc-shaped silicon wafer 201 is diced so as to separately form the plurality of droplet ejecting arrays 27.

Next, a manufacturing method of the droplet ejecting apparatus 2 will be described. The three droplet ejecting arrays 27 are bonded to the solution holding container 22. In this case, a bottom surface, on the same side as the lower surface opening 22a, of the solution holding container 22 is bonded to the warp reduction film 220 of the pressure chamber structure 200 in the droplet ejecting array 27.

Thus, the solution holding container 22 having the three droplet ejecting arrays 27 bonded thereto is bonded to the first surface 21a of the electrical board 21 so that the opening 22a of the solution holding container 22 fits inside the opening 21c of the electrical board 21.

Subsequently, the electrode terminal connector 26 and the terminal portion 131c of the lower electrode 131 and the terminal portion 133c of the upper electrode 133 of the droplet ejecting array 27 are connected to each other by wiring 12. A connection method may be using a flexible cable. An electrode pad of the flexible cable can be electrically connected to the electrode terminal connector 26. The terminal portion 131c and the terminal portion 133c may be electrically connected via an anisotropic conductive film formed by thermocompression bonding.

The control signal input terminal 25 on the electrical board wiring 24 has a shape which can come into contact with a leaf spring connector for inputting a control signal that is output from a control circuit (not illustrated), for example. This forms the droplet ejecting apparatus 2.

FIG. 9 is a plan view of a positional relationship between the nozzles 110, communicating with one solution holding container 22, and the well openings 300 of a 1,536 well microplate 4. The terminal portion 131c and the terminal portion 133c which are connected to the drive element 130 for ejecting the solution from the nozzle group 171 are respectively referred to as a terminal portion 131c-1 and a terminal portion 133c-1. Similarly, the terminal portion 131c and the terminal portion 133c which are connected to the drive element 130 for ejecting the solution from the nozzle groups 172 and 173 are respectively referred to as a terminal portion 131c-2 and a terminal portion 133c-2, and a terminal portion 131c-3 and a terminal portion 133c-3. In this case, the wiring patterns 24a and 24b on the electrical board wiring 24 in FIG. 3 are connected to the terminal portion 131c-1 and the terminal portion 133c-1 of the nozzle group 171. The wiring patterns 24c and 24d of the electrical board wiring 24 are connected to the terminal portion 131c-2 and the terminal portion 133c-2 of the nozzle group 172, and the wiring patterns 24e and 24f of the electrical board wiring 24 are connected to the terminal portion 131c-3 and the terminal portion 133c-3 of the nozzle group 173.

Next, an operation of the above-described configuration will be described. The droplet ejecting apparatus 2 is fixed to the droplet ejecting apparatus mounting module 5 of the solution dropping apparatus 1. When the droplet ejecting apparatus 2 is used, a predetermined amount of the solution is first supplied to the solution holding container 22 from the upper surface opening 22b of the solution holding container 22 by a pipette or the like. The solution is held within the solution holding container 22. The three lower surface openings 22a at the bottom portion of the solution holding container 22 respectively communicate with the three droplet ejecting arrays 27. Each pressure chamber 210 of the three droplet ejecting arrays 27 is supplied with the solution from the solution holding containers 22 via the lower surface openings 22a at the bottom surface of the three solution holding containers 22.

Next, the droplet ejecting apparatus mounting module 5 is moved so that the three nozzle groups 171, 172, and 173 are respectively positioned directly above the interiors of three different well openings 300 of the 1,536 well microplate 4.

In this position, a voltage control signal input to the control signal input terminal 25 is transmitted from the electrode terminal connector 26 to the terminal portion 131c of the lower electrode 131 and the terminal portion 133c of the upper electrode 133. At this time, in response to the voltage control signal applied to the drive element 130, the diaphragm 120 is deformed so as to change the volume of the pressure chamber 210. In this manner, the solution in the nozzle 110 of the droplet ejecting array 27 is ejected as a solution droplet. A predetermined amount of solution is dropped from the nozzle 110 into the three well openings 300 of the microplate 4.

The amount of one droplet ejected from the nozzle 110 is in a range of 2 to 5 picoliters. Therefore, the amount of solution ejected into each well opening 300 can be controlled on the order of pL to µL by controlling the number of ejected droplets.

In the droplet ejecting apparatus 2 according to the first embodiment, one solution holding container 22 communicates with the three nozzle groups 171, 172, and 173, and the three nozzle groups 171, 172, and 173 are respectively located immediately above the interior of the three different well openings 300 of the 1,536 well microplate 4. Accordingly, the solution can be simultaneously dropped into the three well openings 300. In this manner, the dropping time can be shortened to ⅓ compared to a droplet ejecting apparatus in which one solution holding container 22 communicates with only one nozzle group. As a result, even a compound dissolved in a highly volatile solution in the solution holding container 22 can be dropped into every well of the 1,536 well microplate 4 in a short period of time. Therefore, it is possible to provide the droplet ejecting apparatus in which the concentration of the compound in the solution holding container 22 is less changed by the volatilization of the solution contained in the solution holding container 22.

Second Embodiment

Figure 10:
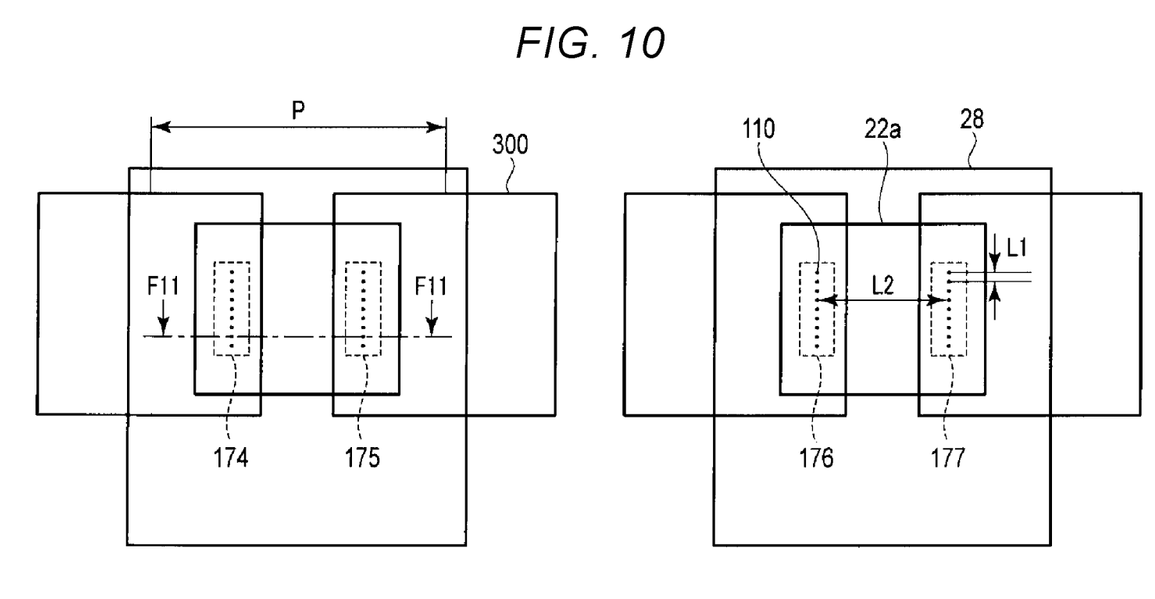
FIG. 10 is a plan view of a position relationship between a nozzle communicating with one solution holding container and a well opening of a 1,536 well microplate in a droplet ejecting apparatus according to a second embodiment.
Figure 11:
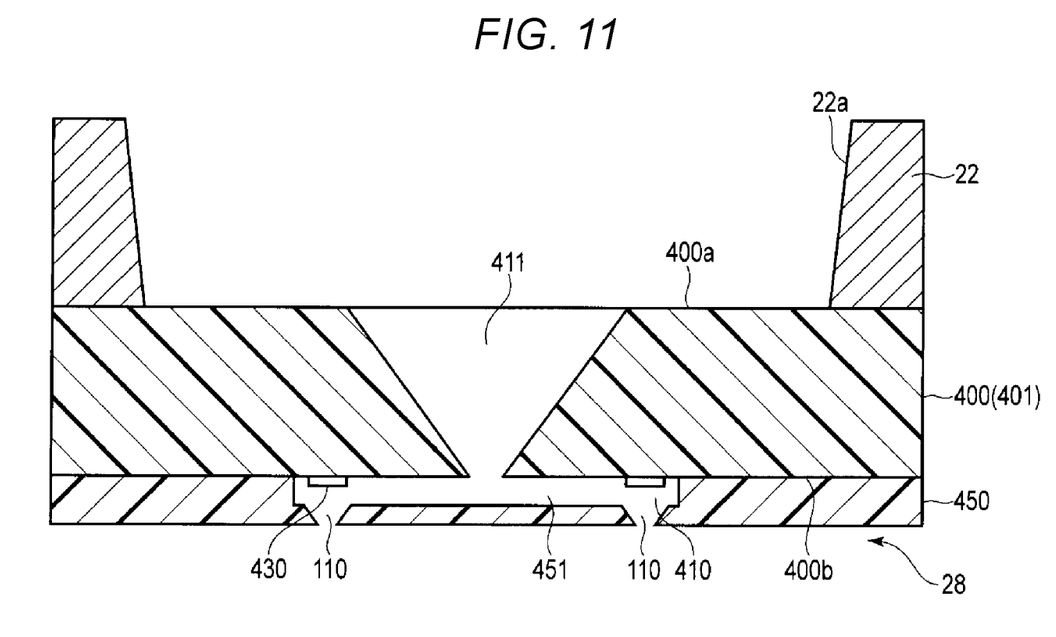
FIG. 11 is a cross-sectional view taken along line F11-F11 in FIG. 10.

FIGS. 10 and 11 illustrate a droplet ejecting apparatus 2 according to a second embodiment. The second embodiment is a modification example in which the configuration of the droplet ejecting apparatus 2 according to the first embodiment, as illustrated in FIGS. 1 to 9, is modified. In the first embodiment, a piezoelectric jet method was described as an example in which the drive element 130 serving as a portion of the actuator is a piezoelectric element, and in which the solution is ejected by the deformation of the drive element 130. In the second embodiment, an actuator uses a thermal jet method.

FIG. 10 is a plan view of a positional relationship between nozzles 110 communicating with one solution holding container 22 of the droplet ejecting apparatus 2 and well openings 300 of the 1,536 well microplate 4. FIG. 11 is a cross-sectional view taken along line F11-F11 in FIG. 10. The same reference numerals are used for the components that are substantially the same as those of the first embodiment, and the description of repeated components may be omitted.

As illustrated in FIG. 11, the droplet ejecting array 28 according to the second embodiment is formed by stacking a silicon board 400 and a photosensitive resin film 450. A front surface side, also referred to as a second surface 400a, of the silicon board 400 has an inlet 411 communicating with the lower surface opening 22a, which serves as the solution outlet of the solution holding container 22. A rear surface side, also referred to as a first surface 400b, of the silicon board 400 has a thin film heater 430 serving as an actuator, and wires (not illustrated) connected to the thin film heater 430.

The photosensitive resin film 450 can be patterned to correspond to a board having a pressure chamber 410 formed thereon. The photosensitive resin film 450 has a flow path 451 communicating with the inlet 411, the pressure chamber 410, and nozzles 110. The pressure chamber 410 is a region where the thin film heater 430 is disposed in the flow path 451. The solution contained in the pressure chamber 410 is heated and boiled by thermal energy generated from the thin film heater 430, thereby ejecting the solution from the nozzles 110.

As illustrated in FIG. 10, two droplet ejecting arrays 28 are bonded to one solution holding container 22 so as to communicate therebetween. The droplet ejecting arrays 28 have nozzle groups 174 and 175 (or 176 and 177) which are arranged in two rows. Here, one set of nine nozzles 110 arranged in a single row is referred to as a nozzle group. Therefore, the four nozzle groups 174, 175, 176, and 177 communicate with one solution holding container 22. In this manner, 36 nozzles 110 communicate with the one solution holding container 22.

When the droplet ejecting apparatus 2 is disposed directly above a the 1,536 well microplate 4, the four nozzle groups 174, 175, 176, and 177, communicating with one solution holding container 22, are inside a well opening 300 of the 1,536 well microplate 4. Therefore, all of the 36 nozzles 110 are disposed within a well opening 300 of the 1,536 well microplate 4 simultaneously. Though, note as depicted in FIG. 10, the nozzle groups 174, 175, 176, and 177 are each above a different one of the well openings 300 of the 1,536 well microplate 4.

A center distance L1 between the adjacent nozzles 110 within nozzle group 174 (alternatively 175, 176, or 177), which are arranged in one row is 0.07 mm. Therefore, the size of nozzle group 174 (alternatively 175, 176, or 177) in the nozzle array direction is 0.56 mm in the X-direction. The size of nozzle group 174 (alternatively 175, 176, or 177) is thus smaller than the size (1.7 mm) of a well opening 300 of a 1,536 well microplate 4.

A distance L2 between the closest nozzles 110 in adjacent nozzle groups 174 and 175, or 176 and 177, is 1 mm. The distance L2 of the closest nozzles 110 between the adjacent nozzle groups 174 and 175 or between the nozzle groups 176 and 177 is thus longer than the distance L1 (0.07 mm) between the adjacent nozzles 110 within nozzle group 174 (alternatively 175, 176, or 177).

Next, an example of a manufacturing method of the droplet ejecting array 28 will be described. The droplet ejecting array 28 is formed on one side surface of the silicon wafer 401 in such a way that a film forming process and a patterning process are repeatedly performed on the thin film heater 430 and wires (not illustrated) connected to the thin film heater 430. A surface having the thin film heater 430 of the silicon wafer 401 and the wires formed thereon is referred to as the first surface 400*b*, and a surface bonded to the lower surface opening 22*a* of the solution holding container 22 on the opposite side is referred to as the second surface 400*a*.

Next, the first surface 400*b* having the thin film heater 430 and the wires formed thereon is coated with a solution containing a precursor of the photosensitive resin G having a polarity different from that of the photosensitive resin film 450 in FIG. 11 by spin coating. Thermal curing is performed by baking, the solvent is removed so as to forma film. Exposure and development are performed on the photosensitive resin G so as to pattern the shape of the flow path 451.

Next, the photosensitive resin G patterned in a shape of the flow path 451 is coated from above with the solution containing the precursor of the photosensitive resin film 450 by spin coating, and thermal curing is performed by baking so as to remove the solvent. The photosensitive resin G and the photosensitive resin film 450 are not compatible since both of these have different polarities. Exposure and development are performed on the photosensitive resin film 450 so as to form the nozzle 110.

Next, the inlet 411 for the solution is formed from the second surface 400*a* side of the silicon wafer 401 by anisotropic etching which uses a tetra methyl ammonium hydroxide (TMAH) solution and which utilizes a difference in an etching rate depending on a silicon crystal orientation. The inlet 411 for the solution opens at an angle of 54.7° with respect to the surface of the second surface 400*a*.

Next, the flow path 451 is formed by dissolving the photosensitive resin G with a solvent. Thereafter, a plurality of the droplet ejecting arrays 28 are separated and formed by dicing the disc-shaped silicon wafer 401. The second surface 400*a* of the silicon wafer 401 of the droplet ejecting array 28 is bonded to the bottom surface, on the same side as the lower surface opening 22*a*, of the solution holding container 22.

Next, an operation according to the second embodiment will be described. The lower surface opening 22*a* on the bottom portion of the solution holding container 22 communicates with the inlet 411 and the flow path 451 of the droplet ejecting array 28. From the lower surface opening 22*a* of the bottom surface of the solution holding container 22, the solution held in the solution holding container 22 fills each pressure chamber 410 in the flow path 451 formed in the photosensitive resin film 450 via the inlet 411 formed in the silicon board 400.

In this position, if a voltage control signal is applied to the thin film heater 430, the heat energy generated from the thin film heater 430 heats and boils the solution contained in the pressure chamber 410. In this manner, the solution is ejected from the nozzle 110 as a solution droplet. A predetermined amount of solution is dropped from the nozzle 110 into the four well openings 300 of the microplate 4.

According to the first embodiment, the distance L1 between the adjacent nozzles 110 within nozzle group 174 (alternatively, 175, 176, or 177) is 0.25 mm. In the second embodiment, the distance L1 is 0.07 mm. Therefore, the second embodiment enables the nozzles 110 to be arranged at a higher density. As a result, one droplet ejecting array 28 can have two nozzle groups 174 and 175 or 176 and 177.

The amount of time required to drop the solution into all well openings 300 of the 1,536 well microplate 4 in the first embodiment and the second embodiment is as follows. In the droplet ejecting apparatus 2 according to the first embodiment, one solution holding container 22 communicates with three nozzle groups 171, 172, and 173, which collectively includes 27 nozzles 110. The droplet ejecting apparatus 2 according to the first embodiment simultaneously drops solution into three well openings 300 (each well receiving droplets from 9 nozzles at once). In the droplet ejecting apparatus 2 according to the second embodiment, one solution holding container 22 communicates with four nozzle groups 174, 175, 176, and 177, which collectively include 36 nozzles 110. The droplet ejecting apparatus 2 according to the second embodiment simultaneously drops the solution into four well openings 300 (each well receiving droplets from 9 nozzles at once). Therefore, the time required to dispense a fixed amount of the solution to all well openings 300 of the 1,536 well microplate 4 by the droplet ejecting apparatus 2 according to the second embodiment can be shortened by 25% of the time by the droplet ejecting apparatus 2 according to the first embodiment.

Each droplet ejecting array 28 according to the second embodiment has two of the four nozzle groups 174, 175, 176, and 177, but has a similar size, 0.56 mm in the X direction, as that of the droplet ejecting array 27 according to the first embodiment which has only one nozzle group, 0.5 mm in the X direction. Accordingly, although the number of the droplet ejecting arrays 28 which can be formed in one silicon wafer 401 is about the same as that according to the first embodiment, the number of the nozzle groups which can be formed on the droplet ejecting arrays 28 is increased. Therefore, the production cost of the droplet ejecting apparatus 2 can be reduced.

According to the second embodiment, similarly to the first embodiment, the droplet ejecting apparatus can simultaneously drop the solution into a plurality of well openings 300 since the solution holding container 22 communicates with a plurality of the nozzle groups. Accordingly, the solution can be dropped into every well of the 1,536 well microplate 4 in a shorter period of time. Therefore, it is possible to provide the droplet ejecting apparatus which reduces the volatilization of the solution contained in the solution holding container 22.

According to the second embodiment, the actuator is the thin film heater 430, and the solution is ejected using a thermal jet method in which the solution is heated and boiled with heat energy generated from the thin film heater 430 so as to use the pressure generated therein.

In the thermal jet method, the solution comes into contact with the thin film heater 430 whose temperature reaches 300° C. or higher. Accordingly, it is preferable to eject only a highly heat-resistant solution which is not degraded even when the temperature reaches 300° C. or higher. Since the thermal jet method employs simpler structure compared to the piezoelectric jet method, the actuator can be miniaturized. Therefore, compared to the piezoelectric jet method, the nozzles can be arranged at a higher density.

In the example embodiments described above, the solution holding container 22 communicates with a plurality of the nozzle groups. Thus, the solution can be simultaneously dropped into a plurality of well openings 300. Accordingly, the solution can be dropped into every well of the 1,536 well microplate 4 in a short period of time. Therefore, it is possible to provide the droplet ejecting apparatus which limits the effect of volatilization of the solution contained in the solution holding container 22.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

For example, the drive element 130 serving as a drive unit has a circular shape. However, the shape of the drive unit is not limited to a circular shape. The shape of the drive unit may be a rhombus shape or an elliptical shape, for example. Similarly, the shape of the pressure chamber 210 is not limited to a circular shape, and may be a rhombus shape, an elliptical shape, or a rectangular shape.

In the example embodiments, the nozzle 110 is disposed at the center of the drive element 130. However, the position of the nozzle 110 is not particularly limited as long as the solution of the pressure chamber 210 can be ejected from the nozzle 110. For example, the nozzle 110 may be formed outside the drive element 130, that is, not within an overlapping region of the drive element 130. If the nozzle 110 is disposed outside the drive element 130, the nozzle 110 does not need to be patterned by penetrating a plurality of film materials of the drive element 130. Likewise, the plurality of film materials of the drive element 130 does not need opening patterning process to be performed at the position corresponding to the nozzle 110. The nozzle 110 can be formed by simply patterning the diaphragm 120 and the protective film 150. Therefore, the patterning process may be facilitated.

What is claimed is:

1. A droplet ejecting apparatus, comprising:
    a solution holding container having a solution inlet for receiving a solution on a first side and a plurality of solution outlets on a second side;
    a plurality of droplet ejecting arrays, each droplet ejecting array being respectively connected to one solution outlet in the plurality of solution outlets;
    a pressure chamber structure on the second side has a plurality of pressure chambers each configured to supply a solution to a corresponding nozzle of the first nozzle group;
    a first nozzle group including a plurality of nozzles in each droplet ejecting array fluidly connected to the respective one solution outlet via the pressure chamber structure; and
    a plurality of actuators in each droplet ejecting array each configured to cause a pressure change in a corresponding pressure chamber in the plurality of pressure chambers to control an ejection of a droplet of the solution from the corresponding nozzle.

2. The droplet ejecting apparatus according to claim 1, wherein
    the droplet ejecting arrays are spaced from each other such that each respective first nozzle group can be positioned above a different well opening of a multi-well plate such that droplets ejected from each respective first nozzle group are received by a respectively different well opening of the multiwell plate.

3. The droplet ejecting apparatus according to claim 1, wherein
    a distance between adjacent nozzles in each first nozzle group is shorter than a distance between first nozzle groups in adjacent droplet ejecting arrays in the plurality of droplet ejecting arrays.

4. The droplet ejecting apparatus according to claim 2, wherein
    the plurality of actuators operate such that droplets of the solution are ejected simultaneously from the plurality of the first nozzle groups.

5. The droplet ejecting apparatus according to claim 1, wherein
    each of the plurality of actuators comprises a piezoelectric film that is configured to deform a pressure chamber in the plurality of pressure chambers and cause the solution to be ejected.

6. The droplet ejecting apparatus according to claim 1, wherein
    each of the plurality of actuators comprises a thin film heater that is configured to heat the solution in one pressure chamber in the plurality of pressure chambers and cause the solution to be ejected.

7. The droplet ejecting apparatus according to claim 1, further comprising:
    a plurality of nozzle groups each including a plurality of nozzles in each droplet ejecting array fluidly connected to the respective one solution outlet via the pressure chamber structure, wherein
    the plurality of pressure chambers are each configured to supply a solution to a corresponding nozzle of a nozzle group in the plurality of nozzle groups, and
    the plurality of actuators in each droplet ejecting array are each configured to cause a pressure change in a corresponding pressure chamber in the plurality of pressure chambers to control an ejection of a droplet of the solution from the corresponding nozzle.

8. The droplet ejecting apparatus according to claim 7, wherein
each nozzle group in each droplet ejecting array is spaced from each other nozzle group such that each nozzle group can be positioned above a different well opening of a multiwell plate such that droplets ejected from each nozzle group are received by a respectively different well opening of the multiwell plate.

9. The droplet ejecting apparatus according to claim 7, wherein
a distance between adjacent nozzles in each nozzle group in each droplet ejecting array is shorter than a distance between adjacent nozzle groups in each droplet ejecting array.

10. The droplet ejecting apparatus according to claim 8, wherein
the plurality of actuators operate such that droplets of the solution are ejected simultaneously from the plurality of the nozzle groups in the plurality of the droplet ejecting arrays.

11. A solution dispenser, comprising:
a base on which a multiwell plate can be disposed; and
a droplet ejector including:
  a solution holding container having a solution inlet for receiving a solution on a first side and a plurality of solution outlets on a second side;
  a plurality of droplet ejecting arrays, each droplet ejecting array being respectively connected to one solution outlet in the plurality of solution outlets; and
  a pressure chamber structure on the second side has a plurality of pressure chambers each configured to supply a solution to a corresponding nozzle of the first nozzle group;
  a first nozzle group including a plurality of nozzles in each droplet ejecting array fluidly connected to the respective one solution outlet via the pressure chamber structure; and
  a plurality of actuators in each droplet ejecting array each configured to cause a pressure change in a corresponding pressure chamber in the plurality of pressure chambers to control an ejection of a droplet of the solution from the corresponding nozzle, wherein
  each droplet ejecting array in the plurality of droplet ejecting arrays is spaced from each other droplet ejecting array such that each respective first nozzle group is disposed so as to be positioned above a different well opening of the multiwell plate.

12. The solution dispenser according to claim 11, wherein the multiwell plate is a one of a 1,536 well microplate, a 3,456 well microplate, or a 6,144 well microplate.

13. The solution dispenser according to claim 11, wherein
the plurality of droplet ejecting arrays are spaced from each other such that at least one well opening of the multiwell plate is between the different well openings of the multiwell plate above which the respective first nozzle groups are respectively disposed.

14. The solution dispenser according to claim 11, wherein
a distance between adjacent nozzles in each first nozzle group is shorter than a distance between first nozzle groups in adjacent droplet ejecting arrays in the plurality of droplet ejecting arrays.

15. The solution dispenser according to claim 11, further comprising:
a plurality of nozzle groups each including a plurality of nozzles in each droplet ejecting array fluidly connected to the respective one solution outlet via the pressure chamber structure, wherein
the plurality of pressure chambers are each configured to supply a solution to a corresponding nozzle of a nozzle group in the plurality of nozzle groups, and
the plurality of actuators in each droplet ejecting array are each configured to cause a pressure change in a corresponding pressure chamber in the plurality of pressure chambers to control an ejection of a droplet of the solution from the corresponding nozzle.

16. The solution dispenser according to claim 15, wherein
each nozzle group in each droplet ejecting array is spaced from each other nozzle group such that each nozzle group can be positioned above a different well opening of the multiwell plate such that droplets ejected from each nozzle group are received by a respectively different well opening of the multiwell plate.

17. The droplet ejecting apparatus according to claim 15, wherein
a distance between adjacent nozzles in each nozzle group in each droplet ejecting array is shorter than a distance between adjacent nozzle groups in each droplet ejecting array.

18. The solution dispenser according to claim 11, wherein
each of the plurality of actuators comprises a piezoelectric film that is configured to deform a pressure chamber in the plurality of pressure chambers and cause the solution to be ejected.

19. The solution dispenser according to claim 11, wherein
each of the plurality of actuators comprises a thin film heater that is configured to heat the solution in one pressure chamber in the plurality of pressure chambers and cause the solution to be ejected.

* * * * *